(12) United States Patent
Bachman et al.

(10) Patent No.: US 10,675,627 B2
(45) Date of Patent: Jun. 9, 2020

(54) FERROMAGNET INFUSED MICROSTRUCTURE ARRAY

(71) Applicant: THE REGENTS OF THE UNIVERSITY OF CALIFORNIA, Oakland, CA (US)

(72) Inventors: Mark Bachman, Irvine, CA (US); Wesley A. Cox-Muranami, San Jose, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 424 days.

(21) Appl. No.: 15/355,009

(22) Filed: Nov. 17, 2016

(65) Prior Publication Data

US 2017/0232436 A1 Aug. 17, 2017

Related U.S. Application Data

(60) Provisional application No. 62/264,492, filed on Dec. 8, 2015, provisional application No. 62/256,654, filed on Nov. 17, 2015.

(51) Int. Cl.
*B01L 3/00* (2006.01)

(52) U.S. Cl.
CPC ... *B01L 3/50855* (2013.01); *B01L 2200/0652* (2013.01); *B01L 2200/12* (2013.01); *B01L 2400/043* (2013.01)

(58) Field of Classification Search
CPC ............... B01L 2200/0652; B01L 2300/0887
USPC ................................................ 422/552, 503
See application file for complete search history.

(56) References Cited

U.S. PATENT DOCUMENTS

| 2006/0194331 A1* | 8/2006 | Pamula | B01F 13/0071 436/150 |
| 2010/0111768 A1* | 5/2010 | Banerjee | C12Q 1/6869 422/82.08 |

* cited by examiner

*Primary Examiner* — Natalia Levkovich
(74) *Attorney, Agent, or Firm* — One LLP

(57) ABSTRACT

Systems and methods directed to an array of microstructures for biological cell sorting with each individual structure component including an integrated magnetic element.

9 Claims, 4 Drawing Sheets

FERROMAGNET INFUSED MICROSTRUCTURE ARRAY

CROSS REFERENCE TO RELATED APPLICATIONS

The present application claims the benefit of priority to U.S. Provisional Application Ser. No. 62/256,654, titled "FERROMAGNET INFUSED MICROSTRUCTURE ARRAY" filed Nov. 17, 2015 and U.S. Provisional Application Ser. No. 62/264,492, titled "FERROMAGNET INFUSED MICROSTRUCTURE ARRAY" filed Dec. 8, 2015, the contents of which are incorporated herein by reference in their entirety.

FIELD

The subject matter described herein relates generally to a biological cell sorting device and, more particularly, to systems and methods directed to an adherent cell sorting platform with individually addressable growth substrates for specified cell release and collection using integrated magnetic structures.

BACKGROUND

The process of retrieving microstructures which have been dissociated from larger arrays, particularly when being used for biological cell sorting, tends to be difficult. Modern methods of cell sorting require chemical or physical removal of selected cells from a larger culture. These cells are then suspended in imaging solution and ran through sorting devices designed to detect physical characteristics of the sorted cells (fluorescent labels, size, etc.). These sorting conditions are especially unfavorable to adherent cell health and viability and can lead to altered cell behavior which can negatively affect research results. Adherent cells primarily make up powerful cells of interest including stem and cancer cells. Researchers working with these cell types in particular greatly benefit from the possibility of sorting and separating specific cells from diverse populations and thus need a platform that is capable of minute cell differentiation while avoiding cell function alteration due to standard sorting platform requirements.

In order to address adherent cell suspension requirement issues, efforts have been made to allow adherent cells to stay in contact with their growth substrates while sorting is being conducted. Automated systems designed to replace manual hand sorting with robot controlled pipettes and scalpels have been developed to selectively remove targeted cells and cell colonies from culture. While these systems help to solve manually intensive sorting protocols, they still rely on old methods of cell capture with the same limitations as hand sorting. These limitations arise from a sorting regime designed by removing small sections of cells from larger samples. These methods inevitably lead to the loss of purity of cells as physically retrieving specific cells from others around them is not trivial. The chemicals used to digest cell connections to their growth surfaces can also cause unwanted alterations to the cell phenotypes post sorting. Instead of trying to automate sorting processes and keeping known flaws, it becomes necessary to design systems that work around these issues. One such solution is the use of microarrays which sequester individual cells onto their own growth surfaces so that collection does not lead to loss of sample purity.

Micro arrays composed of single cell sized structures designed specifically for cell culturing have proven to be powerful tools for cell analysis and sorting by allowing for the physical manipulation of plated cells without the need for chemical digestion from their growth surfaces. These arrays typically composed of patterned, biocompatible photoresist on glass slides are designed to sequester individual cells or cell colonies onto their surfaces in order to separate heterogeneous populations into discrete groups which can be easily separated from one another. When a cell of interest is located on a structure within the array, a laser targeted at the base of the structure is used to eject the individual components from the array. Currently, the most efficient way to collect these components is to invert the entire array over a collection plate, thus utilizing gravity to transfer structures no longer adhered to the glass slide. A major weakness related to this sort of microstructure transfer method is a loss in specificity and purity among captured samples. By relying only on gravity, there is no control over where collected samples actually fall within capture plates and may lead to the unwanted mixing of cells. Methods aimed at solving this issue allow for the individual capture and transfer of released structures, but sacrifices image clarity of samples during analysis. There is a need for a micro array platform which allows for the capture of individual components while also maintaining ideal imaging conditions.

Therefore, it is desirable to provide systems and methods directed to an improved micro array platform which allows for the capture of individual components while also maintaining ideal imaging conditions.

SUMMARY

The various embodiments provided herein are generally directed to systems and methods for a magnet infused microstructure array for adherent cell sorting. An exemplary embodiment includes an array of transparent, microstructures with through holes photolithographically patterned onto a thin film surface formed from an electrically conductive material such as, e.g., gold. Each of the through holes or vias is individually filled with a small selection of ferromagnetic material such as, e.g., gold coated nickel created using a three (3) step electrolytic metal plating process. The exemplary embodiment constrains the through holes or vias and the metal structures contained therein to the corners of the microstructures in order to allow for unhindered imaging of captured samples on the transparent regions. In certain embodiments, vertical chambers such as, e.g., polystyrene vertical chambers, are adhered over the surface of the arrays to allow liquid immersion of the microstructures. The exemplary embodiment utilizes a magnetic probe to individually collect ejected microstructures carrying cell colonies from the array.

According to embodiments, the magnet infused microstructure array is constructed by (1) patterning microstructure arrays on a conductive surface, (2) etching individual structures with through-holes spanning from the top surface to the substrate below, and (3) filling of through-holes with magnetic nickel through electroplating processes.

As noted, the embodiments provided herein include an array of microstructures embedded with internal magnetic components discretely patterned such that the magnets do not greatly impede visibility of the surface of the microstructures. The magnet infused microstructure arrays allow for the direct collection of biological cells adhered to their surfaces without loss in imaging clarity through the structure. The embodiments advantageously allow for the selective individual capture of released array components with only cells of interest on their surfaces enabling simplified sorting and recovery of adherent cells from heterogeneous populations. These structures lead to greater data acquisition, faster cell collection, and more efficient overall adherent cell sorting that the previously described sorting technologies.

Other systems, methods, features and advantages of the example embodiments will be or will become apparent to one with skill in the art upon examination of the following figures and detailed description.

BRIEF DESCRIPTION OF FIGURES

The details of the example embodiments, including structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

It should be noted that elements of similar structures or functions are generally represented by like reference numerals for illustrative purpose throughout the figures. It should also be noted that the figures are only intended to facilitate the description of the exemplary embodiments.

DETAILED DESCRIPTION

Figure 1:
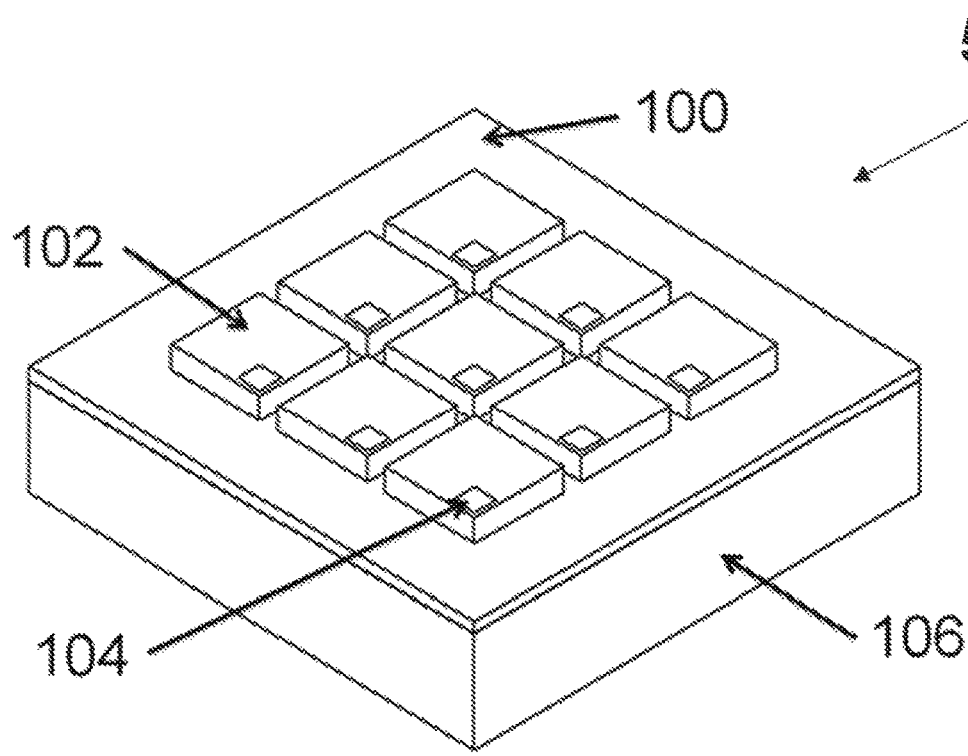
FIG. 1 is an isometric view of an exemplary magnet infused microarray, according to an embodiment of the present disclosure.

Each of the additional features and teachings disclosed below can be utilized separately or in conjunction with other features and teachings to provide systems and methods directed to a magnet infused microarray and its use. Representative examples of the embodiments described herein, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

The various embodiments provided herein are generally directed to systems and methods for a magnet infused microstructure array for adherent cell sorting. An exemplary embodiment includes an array of transparent, microstructures with through holes photolithographically patterned onto a thin film surface formed from an electrically conductive material such as, e.g., gold. Each of the through holes or vias is individually filled with a small selection of ferromagnetic material such as, e.g., gold coated nickel created using a three (3) step electrolytic metal plating process. The exemplary embodiment constrains the through holes or vias and the metal structures contained therein toward the periphery of the microstructure such as, e.g., toward the corners of the microstructures in order to allow for unhindered imaging of captured samples on the transparent regions. In certain embodiments, vertical chambers such as, e.g., polystyrene vertical chambers, are adhered over the surface of the arrays to allow liquid immersion of the microstructures. The exemplary embodiment utilizes a magnetic probe to individually collect ejected microstructures carrying cell colonies from the array.

Referring in detail to the figures, FIG. 1 displays an isometric view of an exemplary magnet infused microarray, according to one embodiment. Microstructures 102 are patterned onto a conductive surface 100 on top of a glass slide 106 by using photolithography. The microstructures 102 are composed of a biocompatible material and are patterned with via holes 104 within their interiors. Via holes 104 span from the conductive layer 100 to the top of each microstructure 102. The microarray 500 is subjected to electrolytic nickel plating to form integrated magnetic elements within the via holes 104 and all other exposed surfaces of the conductive layer 100.

Figure 2:
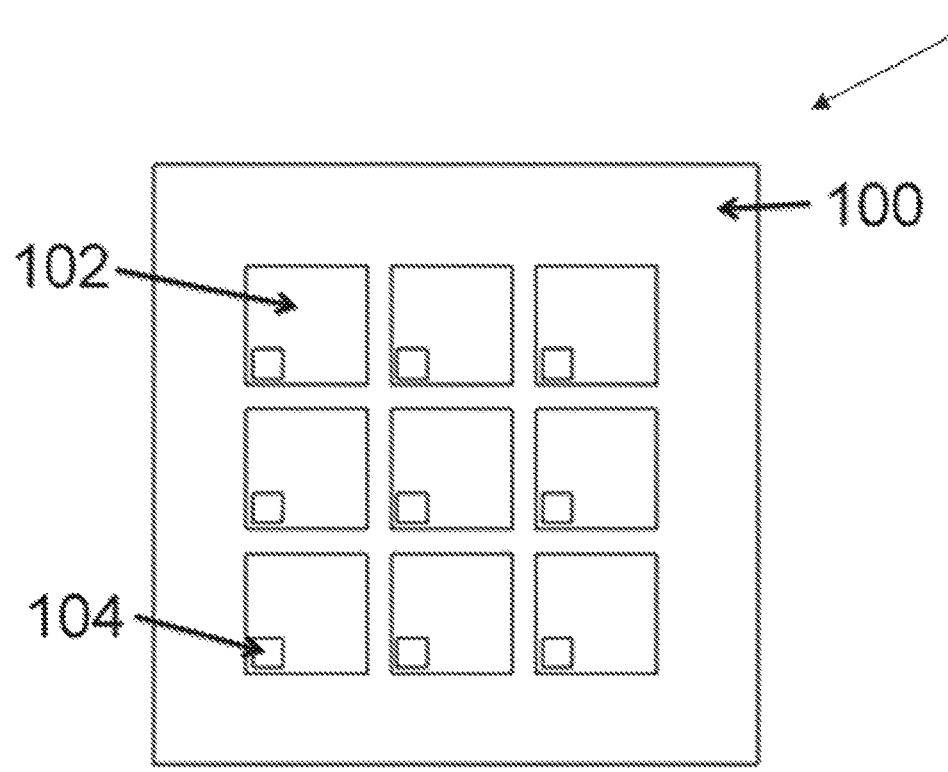
FIG. 2 shows a top view of the magnet infused microarray shown in FIG. 1.

FIG. 2 shows a top view of the magnet infused microarray 500 of FIG. 1. The conductive surface 100 is a transparent conductive patterning surface layered onto a glass slide (not shown). The microstructures 102 are biocompatible microstructures patterned with photolithography. Although shown as having a square shape, the microstructures 102 may have other shapes such as rectangle, hexagon, octagon, circle, oval, and the like. The via holes 104 comprise a ferromagnetic element integrated in the microstructures 102 and, as depicted, are constrained toward the periphery of the microstructure 102 such as, e.g., toward the corners of the microstructures 102 in order to allow for unhindered imaging of captured samples on the transparent regions of the microstructures 102.

Figure 3:
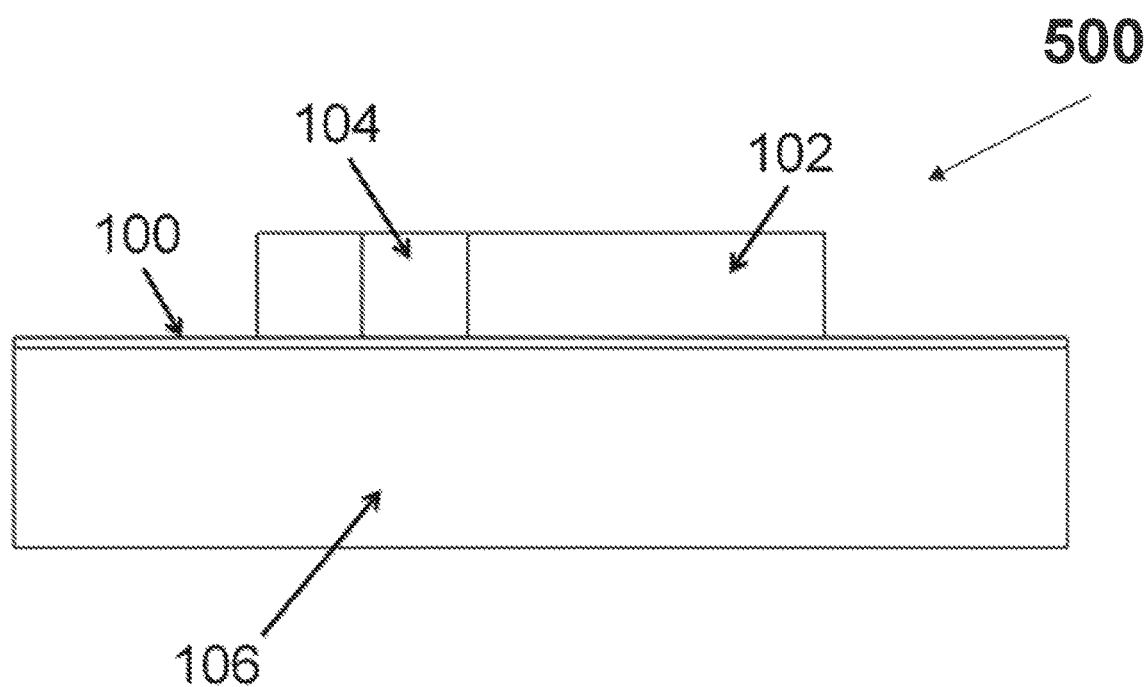
FIG. 3 is a cross sectional view of an individual microstructure and patterning substrate of the magnet infused microarray, according to embodiments of the present disclosure.

FIG. 3 shows a cross-section view of an individual microstructure 102 on a conductive layer 100 deposited on top of a glass slide 106 with a via hole 104 extending from the conductive layer through the entire individual microstructure 102.

Figure 4:
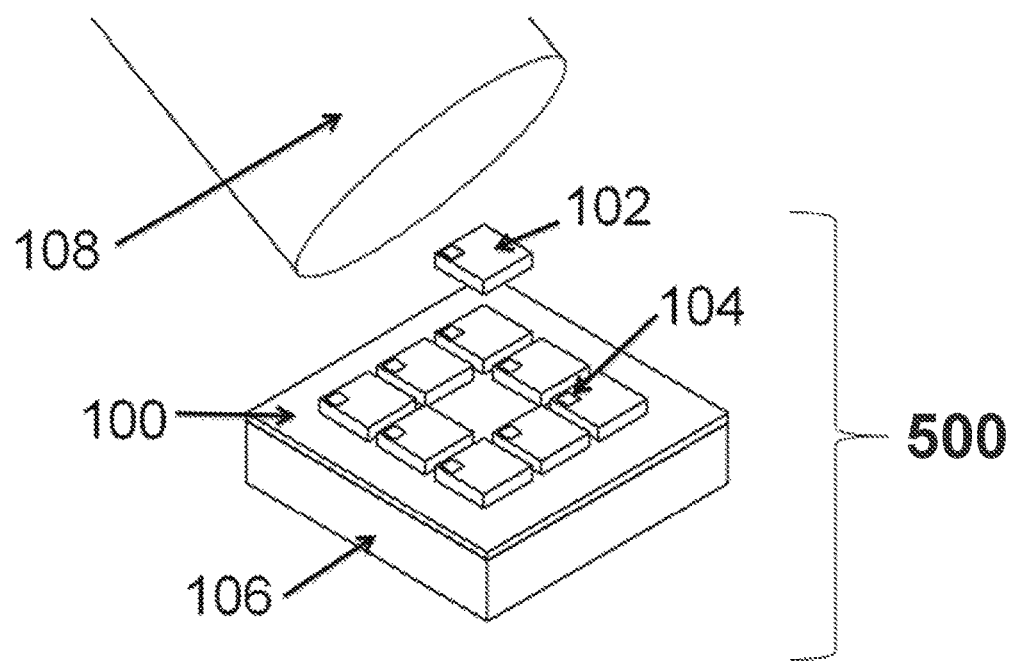
FIG. 4 is an isometric view illustrating a magnetic retrieval of a released microstructure from the magnet infused microarray, according to embodiments of the present disclosure.

FIG. 4 shows a visual concept of the preferred usage of the microarray 500. Once an individual microstructure 102 of the microarray 500 is released, a magnetic probe 108 will be used to attract the microstructure 102. The microstructure 102 can then be freely moved and transferred over to a new culture, away from the microarray 500.

Figure 5:
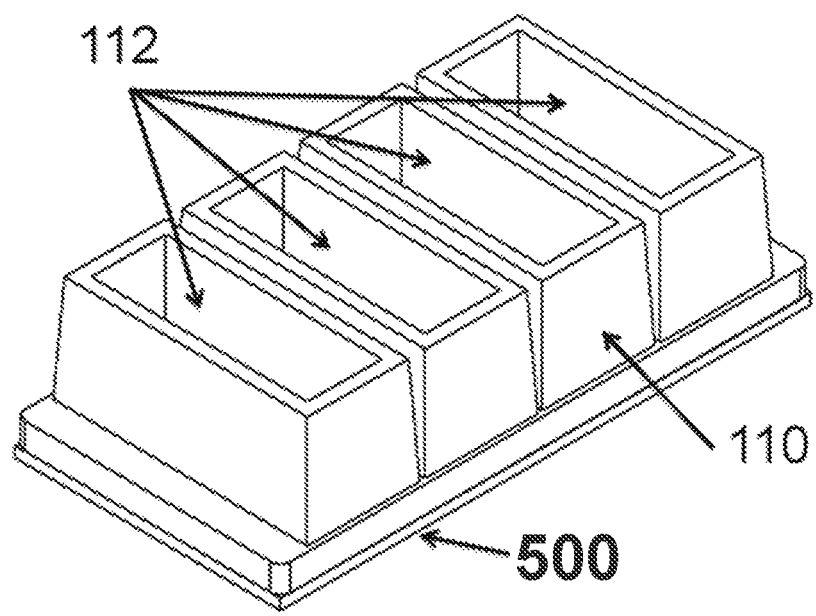
FIG. 5 is an isometric view illustrating an exemplary preparation for use of the magnet infused microarray, according to an embodiment of the present disclosure.

As shown in FIG. 5, a liquid holding chamber slide 110 is adhered to surface of microarray 500. The liquid holding chamber slide 110 includes a set of liquid holding chambers with four separate sections or chambers 112 for cell culture. The vertical chambers 112 are added over each magnet infused microarray 500 to allow for the addition of cell media to culture cells on the array 500.

Figure 6:
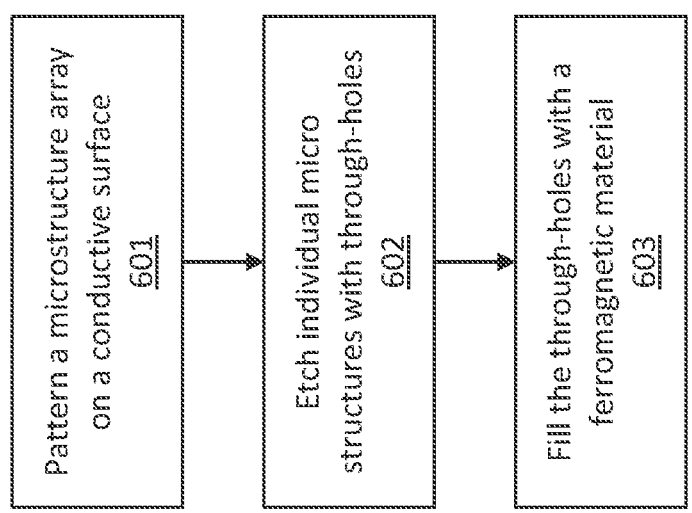
FIG. 6 illustrates an exemplary manufacturing process for use with certain embodiments of the present disclosure.

FIG. 6 illustrates an exemplary manufacturing process for use with certain embodiments of the present disclosure. According to one embodiment, a microstructure array is patterned 601 on a conductive surface. Individual microstructures are etched 602 with through-holes. The through-holes are filled 603 with a ferromagnetic material.

The example embodiments provided herein, however, are merely intended as illustrative examples and not to be limiting in any way.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

In many instances entities are described herein as being coupled to other entities. It should be understood that the terms "coupled" and "connected" (or any of their forms are used interchangeably herein and, in both cases, are generic to the direct coupling of two entities (without any non-negligible (e.g., parasitic intervening entities and the indirect coupling of two entities (with one or more non-negligible intervening entities. Where entities are shown as being directly coupled together, or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed:

1. A magnet infused microarray for cell sorting comprising
   a plurality of microstructures patterned on a conductive surface on top of a transparent substrate, each microstructure having a top and a bottom, wherein the bottom is adjacent the conductive surface;
   a via hole formed in each microstructure of the plurality of microstructures, wherein the via hole is constrained to a corner of the microstructure and spans from the bottom to the top of the microstructure, wherein each microstructure of the plurality of microstructures has a field of view, and wherein the via hole is positioned relative to the field of view, and
   integrated magnetic elements positioned within each of the via holes, wherein the magnetic elements are positioned such that the magnetic elements do not impede the field of view of the microstructure.

2. The microarray of claim 1 wherein the plurality of microstructures is formed of biocompatible material.

3. The microarray of claim 1 wherein the plurality of microstructures are photolithographically patterned onto the conductive surface.

4. The microarray of claim 1 wherein each microstructure of the plurality of microstructures is releasably coupled to the conductive surface of the substrate.

5. The microarray of claim 4, wherein a released microstructure is movable by a magnetic probe.

6. The microarray of claim 1, further comprising a liquid holding chamber slide adhered to the conductive surface of the microarray.

7. The microarray of claim 6 wherein the liquid holding chamber slide comprises one or more liquid holding chambers.

8. The microarray of claim 7, wherein each holding chamber comprises four distinct sections for cell culture.

9. The microarray of claim 1, wherein the via hole is positioned one of outside or toward a periphery of the field of view.

* * * * *